United States Patent [19]
Hitoshio et al.

[11] Patent Number: 4,898,820
[45] Date of Patent: Feb. 6, 1990

[54] PROCESS FOR PRODUCTION OF ISOMALTULOSE

[75] Inventors: Akio Hitoshio; Hisao Takamatsu; Reiko Hattori, all of Tokyo, Japan

[73] Assignee: Showa Denko Kabushiki Kaisha, Tokyo, Japan

[21] Appl. No.: 224,611

[22] Filed: Jul. 27, 1988

[30] Foreign Application Priority Data

Jul. 27, 1987 [JP] Japan ................... 62-185594
Jul. 22, 1988 [JP] Japan ................... 63-181695

[51] Int. Cl.⁴ ............................................ C12P 19/12
[52] U.S. Cl. ................................... 435/95; 435/96; 435/97; 435/98; 435/99; 435/100
[58] Field of Search .................. 435/95, 96, 97, 98, 435/99, 100

[56] References Cited

U.S. PATENT DOCUMENTS 3,865,957  2/1975  Schieweck et al. ............ 426/213
3,912,804 10/1975  Schiweck ........................ 424/9
3,940,481  2/1976  Schiweck ........................ 424/180
4,359,531 11/1982  Bucke et al. .................... 435/97
4,640,894  2/1987  Munir .............................. 435/100
4,670,387  6/1987  Bucke et al. .................... 435/100

FOREIGN PATENT DOCUMENTS 1110189 10/1981 Canada .
1185551  4/1985 Canada .
3528752 10/1986 Fed. Rep. of Germany .
57-10720  2/1982 Japan .
57-94298  6/1982 Japan .
58-38156  8/1983 Japan .
59-2695   1/1984 Japan .
60-9797   3/1985 Japan .
61-249396 11/1986 Japan .
2063268   6/1981 United Kingdom .

Primary Examiner—Herbert J. Lilling
Attorney, Agent, or Firm—Sughrue, Mion, Zinn, Macpeak & Seas

[57] ABSTRACT

A process for the production of isomaltulose whereby glucose and fructose are reacted to form isomaltulose in the presence of an enzyme which hydrolyzes a polysaccharide or oligosaccharide at the α-1,4 and/or α-1,6-glucoside linkage thereof by an exo-type cleavage.

4 Claims, No Drawings

PROCESS FOR PRODUCTION OF ISOMALTULOSE

BACKGROUND OF THE INVENTION

1. Field of the Invention

The present invention relates to a novel process for the production of isomaltulose ($\alpha$-D-glucopyranoside-1,6-fructose). The starting material of the process, i.e., a combination of glucose and fructose, is preferably available, for example, as high fructose syrup (HFS). The product isomaltulose, per se, is used as a non cariogenic sweetener, and is also a starting material for the production of Palatinit (Süddeutsche Zucher AG) which is a low calory sweetener.

Note, Palatinit: an equimolecular mixture of isomers $\alpha$-D-glucopyranoside -1,6- mannitol and $\alpha$-D-glucopyranoside -1,6- glucitol.

2. Description of the Related Art

In known processes for the production of isomaltulose, sucrose is enzymatically converted to isomaltulose. Namely, Japanese Examined Pat. Publication (Kokoku) No. 57-10720 corresponding to DE Nos. 72-2217628, 73-2307251 and 73-2307299 describes a process for the production of isomaltulose by culturing a microorganism belonging to the genus Protaminobacter or Serratia in a sucrose aqueous solution. Japanese Examined Pat. Publication (Kokoku) No. 58-38156 corresponding to DE Nos. 77-2741197 and 78-2806216 discloses a process for the production of isomaltulose from sucrose by continuous fermentation using a microorganism belonging to the genus Protaminobacter. Japanese Examined Pat. Publication (Kokoku) No. 60-9797 corresponding to GB No. 79-7938563; Japanese Unexamined Pat. Publication (Kokai) No. 57-94298 corresponding to DE No. 80-3038219; Japanese Unexamined Pat. Publication (Kokai) No. 59-2695 corresponding to DE No. 82-3213107; and Japanese Unexamined Pat. Publication (Kokai) No. 61-249396 corresponding to DE Nos. 85-3515284 and 85-3528752 disclose processes for production of isomaltulose by placing immobilized microbial cells or an immobilized enzyme in contact with a sucrose aqueous solution.

All the processes described above rely on the conversion of the $\alpha$-1,2 linkage in sucrose to an $\alpha$-1,6 linkage, by an enzyme. Therefore, it is believed that an equilibrium of conversion between sucrose and isomaltulose, is in favor of a production of isomaltulose.

Conversely, it has been believed that a synthesis of isomaltulose from monosaccharides glucose and fructose is disadvantageous from the point of view of the reaction equilibrium, because the reaction forms an ether linkage. Therefore, a process for the production of isomaltulose from glucose and fructose has not been disclosed.

But, since a mixture of glucose and fructose is economically and commercially available as a form of HFS, a process for the production of isomaltulose from a mixture of glucose and fructose, such as HFS or invert sugar, would be commercially advantageous.

Note, "high fructose syrup" (HFS) means a mixture of sugars produced by partially isomerizing a glucose preparation and containing glucose and fructose as main sugar components.

SUMMARY OF THE INVENTION

Accordingly the present invention provides a process for the production of isomaltulose, in which glucose and fructose are reacted to form isomaltulose in the presence of an enzyme which hydrolyzes a polysaccharide or oligosaccharide at the $\alpha$-1,4- and/or $\alpha$-1,6-glucoside linkage thereof by an exo type cleavage.

DESCRIPTION OF THE PREFERRED EMBODIMENT

Generally, enzymes which hydrolyze sugars are classified, for example, according to the following criteria:

(A) a glycosyl residue which is recognized by an enzyme in hydrolysis of a saccharide; for example, a glucosidase recognizes a glucose residue, a galactosidase recognizes a galactose residue, a fructosidase recognizes a fructose residue;

(B) an anomer configuration of an ether linkage to be hydrolyzed; for example, $\alpha$-glucosidase hydrolyzes an $\alpha$-linkage, and $\beta$-glucosidase hydrolyzes a $\beta$-linkage;

(C) an endo-type or exo type; an endo-type enzyme which cleaves a saccharide chain in endogenous fashion, and an exo-type enzyme which sequentially cleaves a saccharide chain from the terminal thereof;

(D) an ether linkage of saccharide to be hydrolyzed; for example, a 1,4-linkage, 1,6-linkage, and 1,3-linkage.

To find the enzyme type which can be used in the present invention, many kinds of enzymes listed as follows have been tested:

(1) invertase ($\beta$-D-fructofranoside fructohydrolase; EC3.2.1.26; exo-type; from yeast)

(2) $\beta$-glucosidase ($\beta$-D-glucoside glucohydrolase; EC3.2.1.21; exo-type; from almond)

(3) $\alpha$-amylase ($\alpha$-1,4-glucan 4-glucanohydrolase; EC3.2.1.1; endo-type; from Bacillus)

(4) dextranase ($\alpha$-1,6-glucan 6-glucanohydrolase; EC3.2.1.11; endo-type; from Penicillium)

(5) isomaltase (oligo $\alpha$-1,6-glucosidase; EC3.2.1.10; exo-type; from yeast)

(6) maltase ($\alpha$-D-glucoside glucohydrolase; EC3.2.1.20; exo-type; from yeast)

(7) $\beta$-amylase ($\alpha$-1, 4-glucan maltohydrolase; EC3.2.1.2; exo-type; from barley)

(8) glucoamylase ($\alpha$-1,4-glucan glucohydrolase; EC3.2.1.3; exo-type; from *Asp. niger*)

(9) glucoamylase ($\alpha$-1,4-glucan glucohydrolase; EC3.2.1.3; exo-type; from Rhizopus)

Each of the above-mentioned enzymes was reacted with glucose and fructose to determine the production of isomaltulose, and the following results were obtained.

| | | Criteria | | | | Reaction Condition | | Production of isomaltulose |
|---|---|---|---|---|---|---|---|---|
| | Enzyme | (A) | (B) | (C) | (D) | pH | Temp. (°C.) | |
| (1) | Invertase | Fr+ | $\beta$ | exo | 1,2 | 4.5 | 55 | — |
| (2) | $\beta$-glucosidase | Gl++ | $\beta$ | exo | 1,4 | 5.0 | 37 | — |
| (3) | $\alpha$-amylase | Gl | $\alpha$ | endo | 1,4 | 6.9 | 20 | — |
| (4) | Dextranase | Gl | $\alpha$ | endo | 1,6 | 6.0 | 37 | — |
| (5) | Isomaltase | Gl | $\alpha$ | exo | 1,6 | 6.8 | 25 | ++ |
| (6) | Maltase | Gl | $\alpha$ | exo | 1,4 | 6.0 | 25 | + |
| (7) | $\beta$-amylase | Gl | $\alpha$ | exo | 1,4 | 4.8 | 20 | ++ |
| (8) | glucoamylase | Gl | $\alpha$ | exo | 1,4 | 4.5 | 55 | +++ |
| (9) | glucoamylase | Gl | $\alpha$ | exo | 1,4 | 4.5 | 55 | +++ |

Fr+ Fructosidase
Gl++ Glucosidase

From the above-mentioned results, it is obvious that the enzymes which can be used in the present process are those which hydrolyze a polysaccharide or oligosaccharide at the α-1,4- or α-1,6-glucoside linkage by an exo-type cleavage.

Enzymes to be used in the process for the production of isomaltulose according to the present invention include, as enzymes which hydrolyze α-1,4-glucoside linkage by an exo-type cleavage, glucoamylase (EC3.2.1.3), β-amylase (EC3.2.1.2), α-glucosidase (EC3.2.1.20), exo-maltotetrahydrolase (EC3.2.1.60), and exo-maltohexahydrolase (EC3.2.1.98); and as enzymes which hydrolyze α-1,6-glucoside linkage by an exo-type cleavage, glucodextranase (EC3.2.1.70), isomaltase (EC3.2.1.10), exo-isomaltohydrolase (EC3.2.1.94), and exo-isomalto-trihydrolase (EC3.2.1.95).

When using the above-mentioned enzymes in the present process, the enzyme can be a purified enzyme preparation or enzyme preparations partially purified to various extents, or crude enzyme-containing preparations. Moreover, in the case of enzymes of microorganism origin, a cultured broth, or living cells separated from a cultured broth, can be used. Moreover, dried cells prepared by a conventional procedure such as drying under a reduced pressure or lyophilization, dried cells dried by dehydration with acetone or ethanol, or disrupted cells, or the like can be used. Enzymes also can be used in a form of an immobilized enzyme or as immobilized cells prepared according to a conventional procedure such as the carrier binding method, the cross-linkage method, the entrapped method, and the like.

All the above-mentioned forms of enzymes are encompassed with the meaning of enzyme as used in this specification and claims.

Although a ratio of glucose and fructose as starting materials is not critical, too high a ratio of glucose to fructose results in a preferential production of malto-oligosugar such as maltose, isomaltose, etc., and too high a ratio of fructose to glucose results in a decrease of a total amount of oligosugars. Therefore, according to the present invention, a ratio of glucose to fructose is 1:100 to 100:1 by weight, preferably 1:10 to 10:1, more preferably 1:2 –2:1, and most preferably 1:1.

The starting materials, i.e., a mixture of glucose and fructose can be prepared by mixing glucose and fructose, but HFS or high fructose HFS is preferable because it contains glucose and fructose in a preferable ratio, as described above, and is economically and commercially available. Alternatively, invert sugar can be used.

The concentration of enzymes in a reaction mixture depends on the concentration of substrates, i.e., glucose and fructose To force an equilibrium of a reaction to the direction for isomaltulose formation, preferably the concentrations of the sugars are relatively high. For example, a concentration of at least one of glucose and fructose is preferably 5 to 100 W/V %, and under such a condition, the concentration of enzyme is preferably at least 10 units/ml, more preferably at least 100 units/ml. Note, the higher the concentration, the shorter the reaction time.

The reaction temperature and pH value of a reaction medium in the present process may be similar to those for a hydrolysis reaction of a particular enzyme, and depend on the particular enzyme. For example, for glucoamylase, the pH value of the reaction medium is preferably about 3.5 to 8.0; for β-amylase, the pH value is preferably about 4.0 to 7.0; and for isomoltase, the pH value is preferably about 4.5 to 8.0. A temperature for the reaction is preferably higher, to an extent wherein an enzyme used is not inactivated. For example, for glucoamylase, the reaction temperature is preferably a room temperature to about 80° C.; for β-amylase, the reaction temperature is preferably a room temperature to about 50° C.; and for isomaltase, the reaction temperature is preferably a 20 to about 40° C. Generally, the optimum conditions of enzymes, such as the optimum pH, optimum temperature, thermostability, etc., are different according to the particular enzymes, especially when considering their origin, and these conditions are already reported or easily can be determined by simple experiments.

To maintain a pH of a reaction medium at a constant value, the reaction medium is preferably a buffer solution. Preferable buffers include citrate buffer, phosphate buffer, acetate buffer, glycine buffer, and the like. The reaction is usually carried out in an aqueous medium, but since the reaction of the present process is a condensation reaction resulting in a release of water, the reaction may be also carried out in an organic medium such as ethanol, methanol, acetone, etc.

The reaction of the present process can be carried out batchwise, or when an immobilized enzyme or immobilized cells are used, the reaction can be carried out continuously using a column filled with the immobilized preparation. The reaction time depends on the substrate concentration, enzyme concentration, and type of reaction process. Normally, for a batchwise reaction, the reaction time about 5 hours to 200 hours, but is shorter for a continuous reaction using a column.

The process for recovery and purification of isomaltulose from a reaction mixture is carried out according to any of the well-established conventional procedures used for industrial separation and purification for other oligo-sugars, such as filtration or centrifugation to eliminate solid impurity, ion exchange for purification, concentration and crystallization to recover a solid product, and the like.

In the enzyme reaction according to the present invention, not all substrates are converted to isomaltulose, and thus a spent medium containing residual substrates, i.e., glucose and/or fructose remaining after a recovery of isomaltulose from a reaction medium, is preferably reused. In this case, the spent medium to be reused can be supplemented with glucose and/or fructose.

A reaction mixture of the present process was analyzed by, for example, a method of M. Ghebregzabher et al., J. Chromatography, Vol 180, 1–16, 1979, thin layer chromatography. In this method, one µl of a sample was spotted on a thin layer Kiesel Gel 60 $F_{254}$ plate (Merck), and the plate was subjected to two-dimensional thin layer chromatography using, as a developing system, a developing solvent comprising methyl ethyl ketone, 2-propanol, acetonitrile, 0.5 M boric acid and 0.25 M isopropyl amine (2:3:1:1), and a developing solvent comprising methyl ethyl ketone, dipropyl ether, 2-propanol, pyridine, water and phenyl boric acid (2:1:3:1:1:1), and color development was carried out by a mixture of 2% diphenylamine and 2%, aniline dissolved in acetone, and phosphoric acid (1:1:8.5). Under the above conditions, the isomaltulose was completely separated from glucose, fructose, maltose, isomaltose, torehalose, sucrose, maltulose and the like, and clearly detected. Alternatively, the isomaltulose can be analyzed by high performance liquid chromatography using a commercially available column for the separation of sugars.

EXAMPLES

The present invention will now be further explained by, but is by no means limited to, the following examples.

EXAMPLE 1

6100 units of glucoamylase of *Asp. niger* origin were added to 5 ml of a reaction mixture of a citric acid-sodium citrate buffer (pH 4.5) containing 10% glucose and 30% fructose, and a reaction was carried out at 65° C. overnight. The yield of isomaltulose formed during the reaction was 46% in relation to the glucose added. Note, the isomaltulose was determined according to the following procedure: The reaction mixture was filtrated by a ultrafiltration membrane to eliminate proteins, and the filtrate was diluted 6 to 10 fold. One $\mu$l of the diluted sample was spotted on a thin layer Kiesel Gel 60F$_{254}$ plate (Merck), and the plate was subjected to two-dimensional thin layer chromatography using, as a developing solution, a mixture of methyl ethyl ketone, 2-propanol, acetonitrile, 0.5 M boric acid, and 0.25 M isopropylamine dissolved in acetic acid (2:3:1:1), and a mixture of methyl ethyl ketone, dipropyl ether, 2-propanol, pyridine, water and pheny boric acid (2:1:3:1:2.4). The plate was then treated with a mixture of 2% diphenylamine and 2% aniline dissolved in acetone, and phosphoric acid (1:1:8.5) to detect the isomaltulose by color development. Further, the reaction mixture was analyzed by high performance liquid chromatography using Shodex DC 613 column or Shodex SZ 5532 column (Showa Denko, Japan)

EXAMPLE 2

840 units of isomaltase of yeast origin was added to 0.5 ml of a reaction mixture of a citric acid-disodium phosphate buffer (pH 6.0) containing 10% glucose and 30% fructose, and the reaction was carried out at 30° C. overnight. The yield of the isomaltulose formed during the reaction was 17%, in relation the glucose added. Note, the isomaltulose was determined according to the same procedures as described in Example 1.

EXAMPLE 3

8400 units of $\beta$-amylase of barley origin were added to 5 ml of a reaction mixture of a citric acid-disodium phosphate buffer (pH 4.8) containing 10% glucose and 30% fructose, and the reaction was carried out at 25° C. overnight. The yield of the isomaltulose formed during the reaction was 15%, in relation to glucose added. Note, the isomaltulose was determined according to the same procedures as described in Example 1.

REFERENCE EXAMPLE 8400 each of invertase of yeast origin, $\beta$-glucosidase of almond origin, $\alpha$-amylase of Bacillus origin, and dextranase of Penicillium origin were separately added to 5 ml of a reaction mixture of a citric acid-disodium phosphate containing 10% glucose and 30% fructose, and the reaction was carried out overnight. An optimum pH and optimum temperature set forth in the above-mentioned table were used for the corresponding enzyme. The reaction mixtures were analyzed according to the same procedures as described in Example 1.

Although $\beta$-glucosidase provided a remarkable amount of oligosugars, isomaltulose was not detected. The other three enzymes did not show the formation of isomaltulose.

We claim:

1. A process for production of isomaltulose characterized by reacting glucose and fructose to form isomaltulose in the presence of an enzyme which hydrolyzes a polysaccharide or oligosaccharide at the $\alpha$-1, 4- and/or $\alpha$-1,6-glucoside linkage thereof by an exo-type cleavage.

2. A process according to claim 1 wherein the enzyme is selected from the group consisting of glucoamylase, $\beta$-amylase, $\alpha$-glucosidase, exo-maltotetrahydrolase, exo-maltohexahydrolase, glucodextranase, isomaltase, exo-isomaltohydrorase, and exo-isomaltotrihydrolase.

3. A process according to claim 1, wherein glucose and fructose are used as a high fructose syrup or a invert sugar.

4. A process according to claim 1 wherein the reaction is carried out under an optimum pH and temperature for hydrolysis by a corresponding enzyme.

* * * * *